(12) United States Patent
Alby

(10) Patent No.: US 7,422,597 B1
(45) Date of Patent: Sep. 9, 2008

(54) IMPLANT FOR OSTEOSYNTHESIS DEVICE AND TOOL FOR SETTING SUCH IMPLANT

(75) Inventor: Albert Alby, Paris (FR)

(73) Assignee: Scient'x Societe A Responsabilite Limitee, Parks (FR)

( * ) Notice: Subject to any disclaimer, the term of this patent is extended or adjusted under 35 U.S.C. 154(b) by 0 days.

(21) Appl. No.: 09/380,614

(22) PCT Filed: Mar. 18, 1998

(86) PCT No.: PCT/FR98/00543

§ 371 (c)(1),
(2), (4) Date: Jan. 7, 2000

(87) PCT Pub. No.: WO98/41159

PCT Pub. Date: Sep. 24, 1998

(30) Foreign Application Priority Data

Mar. 18, 1997 (FR) .................................. 97 03277

(51) Int. Cl.
*A61B 17/70* (2006.01)
(52) U.S. Cl. ...................... 606/246; 606/301
(58) Field of Classification Search .................. 606/61, 606/72, 73, 99, 104; 411/419
See application file for complete search history.

(56) References Cited

U.S. PATENT DOCUMENTS

| 2,102,881 A | * | 12/1937 | Blackburn et al. | .......... 439/779 |
| 5,261,912 A | * | 11/1993 | Frigg | .......... 606/61 |
| 5,466,237 A | * | 11/1995 | Byrd et al. | .......... 606/61 |
| 5,554,157 A | * | 9/1996 | Errico et al. | .......... 606/61 |
| 5,681,319 A | * | 10/1997 | Biedermann et al. | .......... 606/104 |
| 5,716,356 A | * | 2/1998 | Biedermann et al. | .......... 606/61 |
| 5,873,878 A | * | 2/1999 | Harms et al. | .......... 606/61 |
| 5,941,885 A | * | 8/1999 | Jackson | .......... 606/104 |
| 6,565,565 B1 | * | 5/2003 | Yuan et al. | .......... 606/61 |
| 6,896,677 B1 | * | 5/2005 | Lin | .......... 606/61 |
| 7,081,116 B1 | * | 7/2006 | Carly | .......... 606/61 |

FOREIGN PATENT DOCUMENTS

| DE | 196 05 640 | 8/1997 |
| EP | 0 528 706 | 2/1993 |
| EP | 672388 A1 * | 9/1995 |
| EP | 0 682 918 | 11/1995 |
| WO | WO 93 11715 | 6/1993 |

* cited by examiner

*Primary Examiner*—Eduardo C. Robert
*Assistant Examiner*—Nicholas Woodall
(74) *Attorney, Agent, or Firm*—Bacon & Thomas, PLLC

(57) ABSTRACT

The present invention concerns an implant for an osteosynthesis device in particular of the backbone and the specific tool for setting this implant, enabling a secure fixing and a simple and easy setting.

The implant comprises a bone anchoring device (1) topped with a fixing head (3) consisting of two side branches (5) forming an open U and designed to receive a linking rod to be locked by clamping, by means of a threaded nut (6) to be screwed on matching threaded parts produced on the partially cylindrical outer walls (5a) of the fixing head (3) side branches, and comprises, in the nut (6) diametral zone, a plate mounted in free rotation.

The implant, in combination with the corresponding tool, enables the setting with blind indexing of the plate between the U-shaped branches (5) of said head (3), before and during the clamping of the nut, which is performed with the same tool (10).

5 Claims, 3 Drawing Sheets

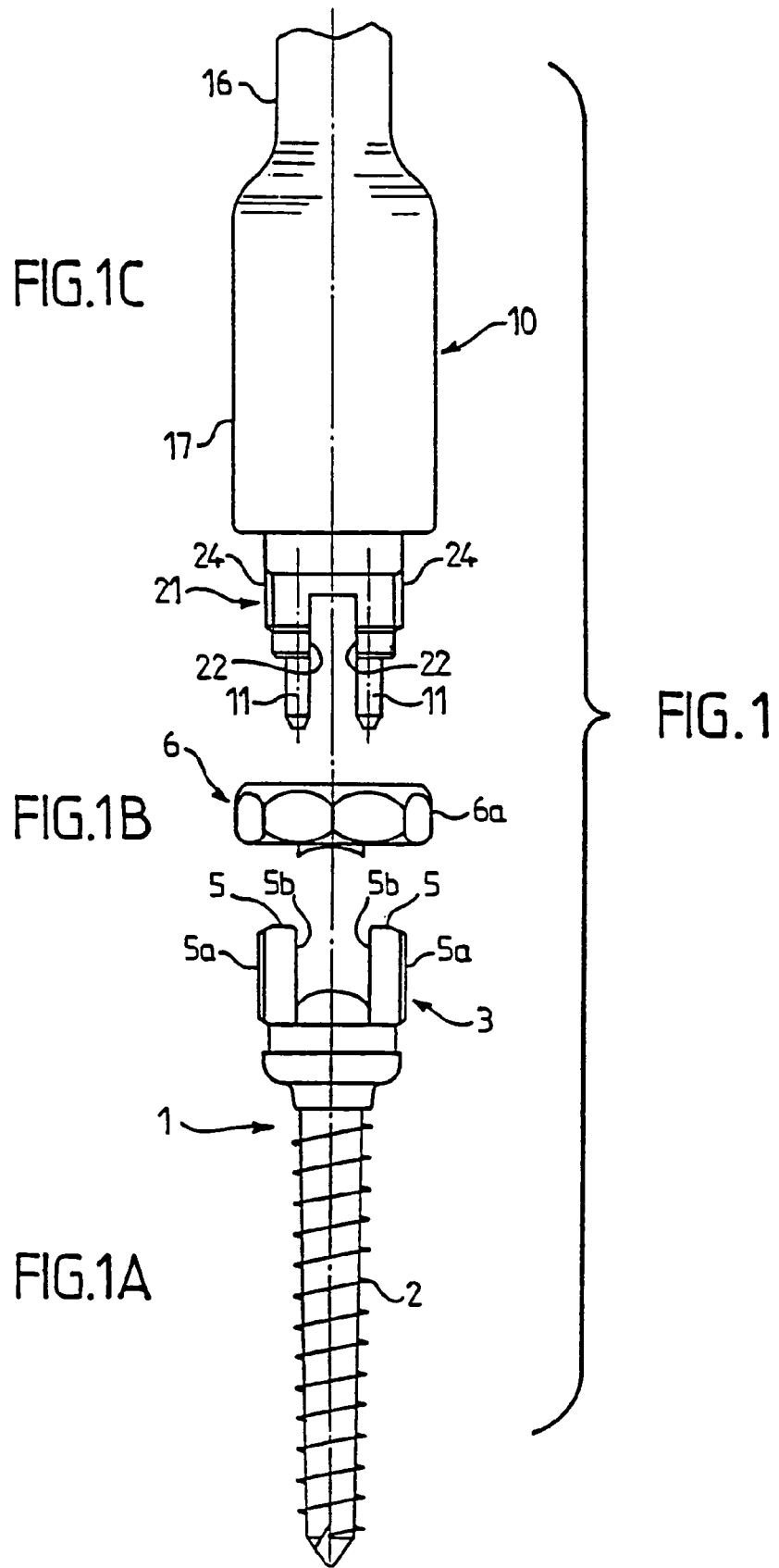

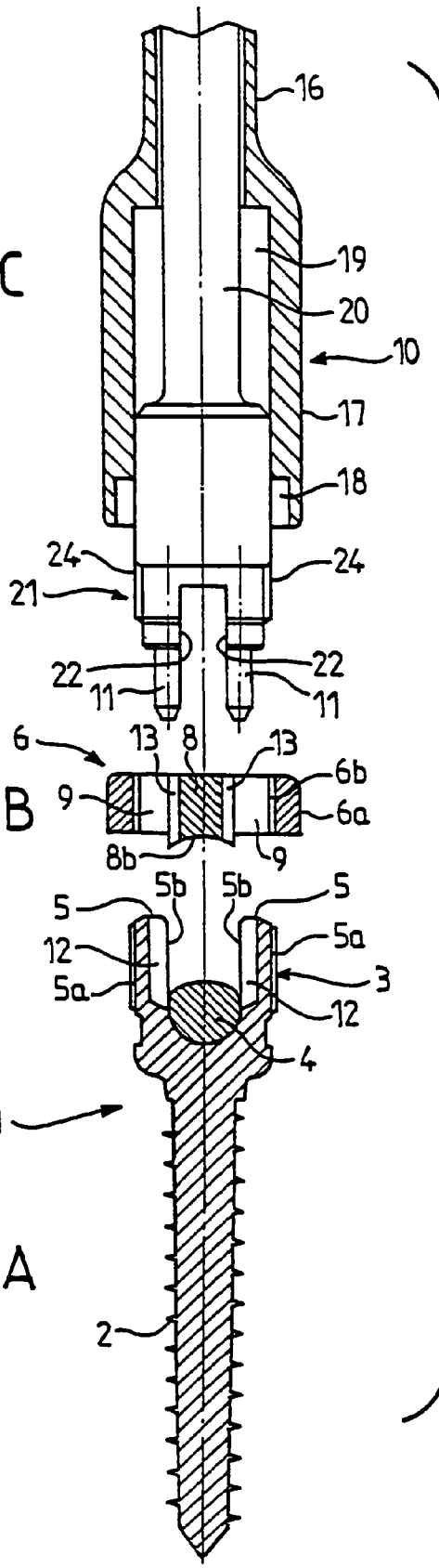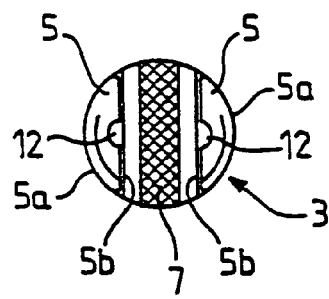

IMPLANT FOR OSTEOSYNTHESIS DEVICE AND TOOL FOR SETTING SUCH IMPLANT

TECHNICAL FIELD

The present invention relates to an implant for osteosynthesis device, particularly of the backbone, comprising a bone anchoring device topped by a fixing head constituted by two lateral branches forming an open U and intended to receive a linking rod with a view to inmobilization thereof by clamping via a threaded nut adapted to screw on corresponding threaded parts produced on the outer walls of the lateral branches of the fixing head.

Different implants of which the fixing body comprises lateral branches forming a channel for receiving a linking rod, have been described.

PRIOR ART TECHNIQUE

For example, in French Patent Application No. 2 711 909, the lateral branches of the U forming the head are threaded, not only on the outside, but also on the inside, in order to receive a conical plug intended to space the branches apart in order to immobilize the nut.

In this device, it is necessary to engage the nut by hand on the outer threading of the head, then the plug in the inner threading of the bone anchoring device in place on the patient before effecting definitive blocking thereof via two distinct appropriate tools.

This device, of relatively simple design, is easy to carry out, but it is necessary to use two tools and previously to engage the nut and the plug in their corresponding threading by hand, this being effected with a certain trial and error method and under unfavourable conditions by reason of execution during a surgical operation.

It has been proposed, in European Patent Application No. 0 528 706 or in French Patent No. 2 658 414, to effect clamping of the rod via an auxiliary bearing element intended to be previously inserted between the branches of the fixing head in order to ensure a better contact with the rod.

In that case, the additional difficulty consists in the manipulation of the intermediate bearing element which it is necessary to insert between the parallel branches of the fixing head.

It will be understood that this difficulty of centering the bearing element would be further increased if the bearing element were rendered fast with the nut, since the practitioner had to both feel around for the indexing of the bearing element, hidden by the nut, and screw the nut on the head, blind.

It is an object of the invention to overcome the different drawbacks set forth hereinabove by proposing a device allowing a solid fixation and simple and easy positioning of a bearing element for a linking rod.

STATEMENT OF THE INVENTION

The invention relates to an implant for osteosynthesis device of the backbone, comprising a bone anchoring device topped by a fixing head constituted by two lateral branches forming an open U and designed to receive a linking rod with a view to immobilization thereof by clamping, via a threaded nut adapted to screw on corresponding threaded parts produced on the partially cylindrical outer walls of the lateral branches of the fixing head, characterized in that the nut comprises, in its diametral zone, a plate mounted in free rotation.

The width of the plate is adapted to allow slide of said plate between the branches of the fixing head, defining two lateral clearances on either side of said plate for the passage of the branches of the U inside the nut and the insertion of the two pins of an auxiliary tool for gripping the nut in order to facilitate mounting thereof on the fixing head.

The fixing head comprises two grooves made opposite on the inner walls of these branches of the U in order to ensure, after mounting of the rod, the guiding of the pins of the tool on the head and, consequently, a blind indexing of the plate between the branches of the U of said head, before and during clamping of the nut which supports it, clamping being effected via the same tool.

The present invention also concerns the characteristics which will emerge in the course of the following description which will have to be considered separately or in all of their possible technical combinations.

BRIEF DESCRIPTION OF THE DRAWINGS

This description, given by way of non-limiting example, will show more clearly how the invention may be carried out, with reference to the accompanying drawings, in which:

FIG. 1 is an exploded view on a double scale of an implant in accordance with an embodiment of the invention and of an associated tool intended for setting it, views 1A, 1B, 1C respectively representing an anchoring device, a nut, a tool, of which only the end has been shown.

FIG. 2 is a view in longitudinal section of FIG. 1, views 2A, 2B, 2C respectively showing the anchoring device, the nut, the tool.

FIG. 3 is a plan view of the anchoring device.

BEST MANNER OF IMPLEMENTING THE INVENTION

Figure 4:
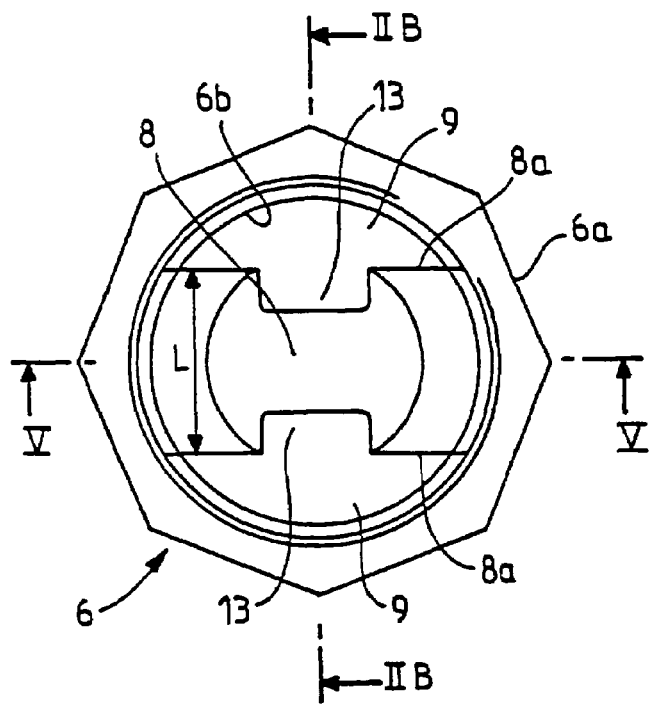
FIG. 4 is a plan view of the nut.

The implant shown in FIGS. 1A and 1B is constituted by a bone anchoring device 1 comprising a self-tapping pedicular screw known per se, composed of a threaded part 2 with wide screw pitch, intended to be screwed in the bone, and a visible upper part constituting a fixing head 3 for a rod 4 for linking between two successive bone anchoring devices 1.

The fixing head 3 is constituted by two lateral branches 5 forming an open U intended to receive the linking rod 4.

The outer faces 5a of the branches 5 are inscribed in a cylinder and are threaded in order to receive a corresponding threaded nut 6 adapted to be screwed on the head 3 with a view to clamping on the rod 4, once in place.

The rod 4 is cylindrical and it is also knurled over the whole of its outer surface, so as to avoid slidings after clamping and in order to improve immobilization of said rod.

The bottom 7 of the U formed by the fixing head 3 presents a radius corresponding substantially to that of the rod 4 and is also knurled.

The clamping nut 6 presents, as known per se, a hexagonal outer cross-section 6a in order to allow it to be gripped by a corresponding tool and comprises a threaded cylindrical inner part or tapping 6b intended to be screwed on the threaded part of the head 3 of the bone anchoring device 1.

The nut 6 comprises, in its diametral zone, a plate 8 mounted to rotate freely, of which the width L is such that it allows axial slide thereof between the branches 5 of the U of the fixing head 3, while defining with respect to said nut 6, two lateral clearances 9 intended, on the one hand, for the passage of the branches 5 of the head 3, during screwing of the nut 6, and, on the other hand, for the insertion of two pins 11 of an auxiliary tool 10 for gripping said nut 6, in order to facilitate assembly thereof on the fixing head 3.

The inner walls 5*b* of the opposite branches 5 of the fixing head 3 comprise two grooves 12 at the centre of said walls.

These grooves serve to ensure, after positioning of rod 4, the guiding of the pins 11 of the tool 10 on the head 3 and, consequently, a blind indexing of the plate 8 between the branches 5 of the U of the head 3, before and during clamping of the nut 6 which supports it. The nut 6 is clamped via the same tool 10.

According to another characteristic of the invention, the plate 8 comprises, on its lateral edges 8*a*, two notches 13 each forming part of a lateral clearance 9. The notches 13 define, in complement and in cooperation with the guiding grooves 12 of the branches 5 of the fixing head 3, housings 12/13 intended for the introduction and positioning of the pins 11 of the tool 10. As illustrated in the drawings, the width L of the plate 8 taken perpendicularly to the diametral direction of the nut 6, presents a value for example substantially equal, apart from the notches 13, to the spacing between the branches 5 of the fixing head 3.

According to another characteristic of the invention, the surface of the plate 8*b* is concave and congruent of the surface of the cylindrical rod 4 and knurled for a better adherence on said rod 4.

Figure 5:
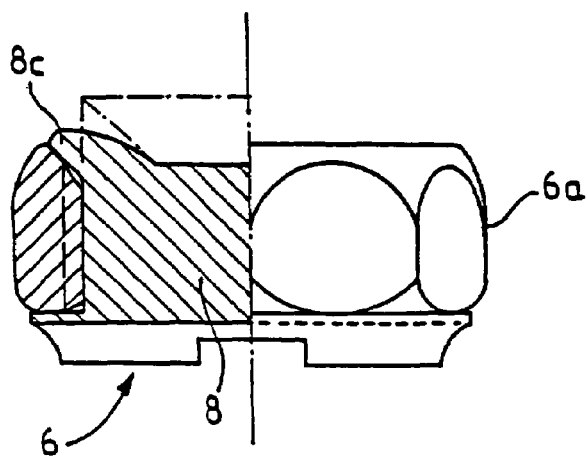
FIG. 5 is a side view of the nut of which half is a section along line V-V of FIG. 4.

The plate 8 is fixed to rotate freely on the nut 6 by an adequate crimping 8*c* (FIG. 5).

According to the embodiment shown, the bone anchoring device is a pedicular screw but, of course, it may be question of any other means, such as for example a hook.

It should also be noted that all the elements which have just been described and constituting the implant, are made of a titanium alloy or equivalent material of which the amagnetic properties do not create artefacts during IRM or scanner examinations.

Figure 6:
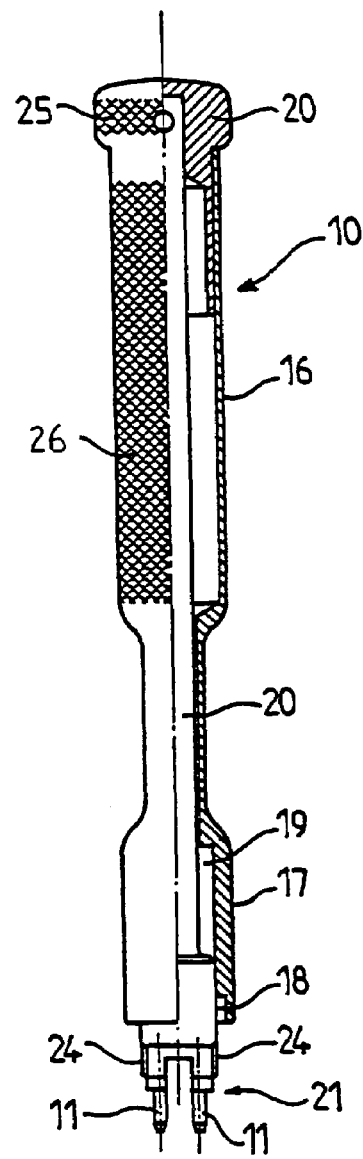
FIG. 6 is a view on scale 1 of a setting tool, shown partially in section.

The invention also concerns the particular structure of the auxiliary tool 10. As shown particularly well in FIGS. 1C, 2C and 6, said tool is constituted by a cylindrical sleeve 16 comprising an end part 17, forming a female hexagonal endpiece 18, adapted to cooperate with the nut 6 of the implant and in which opens out a bore 19 intended for axial slide of a sliding member 20.

The sliding member 20 comprises an emerging end 21 constituted by two partially cylindrical lateral branches 22 forming an open U and of which the outer walls 24 are threaded so as to allow prior screwing of the nut 6 on the tool, while allowing free slide of the plate 8 of said nut between said threaded branches 22 of this same tool 10.

In this way, the nut 6, previously screwed on the branches 22 of the tool 10, may, after its positioning on the fixing head 3 via the pins 11 in the grooves 12 of the branches 5 of said head, be transferred directly from the threading 24 of the tool 10 to the threading 5*a* of the head 3. Transfer is effected via the hexagonal endpiece 18 actuated in rotation by the operator, while immobilizing the sliding member likewise by rotation.

The nut 6 will be rotated until it is blocked on the rod 4 via the plate 8.

For a better grip of the tool 10, the upper zone 26 of the cylindrical sleeve 16 and the upper end 25 of the sliding member 20 are knurled.

The invention claimed is:

1. Implant for osteosynthesis device particularly of the backbone, comprising
    a bone anchoring device topped by a fixing head comprising two lateral branches forming an open U and configured to receive a linking rod, and
    a threaded nut adapted to screw on corresponding threaded parts produced on partially cylindrical outer walls of the lateral branches of the fixing head,
    wherein the nut comprises a plate mounted completely within a diameter of an open cylindrical inner part of the nut, the plate being in free rotation in and extending diametrically across the open cylindrical inner part, the plate having a width such that two lateral clearances are defined on either side of said plate in order to allow passage of the branches of the fixing head inside the nut whereby the plate is allowed to slide between the branches;
    wherein said two lateral clearances are configured and dimensioned to receive, when the lateral branches of the fixing head are engaged in said lateral clearances, two pins of an auxiliary tool for gripping the nut in order to facilitate assembly of the nut on the fixing head.

2. Implant for osteosynthesis device according to claim 1, wherein the fixing head comprises two grooves made opposite on the inner walls of the U-shaped branches in order to ensure, after assembly of the rod, the guiding of pins of a tool on the fixing head and a blind indexing of the plate between the U-shaped branches of said head, before and during clamping of the nut which supports it, via the same tool.

3. Implant for osteosynthesis device according to claim 2, wherein the plate comprises, on its lateral edges, two notches defining, in complement and in cooperation with the guiding grooves of the U-shaped branches of the fixing head, housings intended for the introduction and positioning of pins of a tool.

4. Implant for osteosynthesis device according to claim 3, wherein the notches form, in the edges of the plate, quadrangular baffles intended for housing the extensions of the pins of a tool.

5. Implant for osteosynthesis device according to claim 3, wherein the surface of the plate is concave and congruent of the surface of the cylindrical rod and knurled for a better adherence on said rod.

* * * * *